United States Patent [19]

Miyano

[11] 3,932,467

[45] Jan. 13, 1976

[54] PROCESS FOR THE PRODUCTION OF 2β-FORMYL 3α-PROTECTED HYDROXY-5-OXOCYCLOPENTANE-1α-HEPTANOIC ACIDS AND ESTERS CORRESPONDING

[75] Inventor: Masateru Miyano, Morton Grove, Ill.

[73] Assignee: G. D. Searle & Co., Chicago, Ill.

[22] Filed: Aug. 28, 1973

[21] Appl. No.: 392,317

Related U.S. Application Data

[63] Continuation-in-part of Ser. No. 187,853, Oct. 8, 1971, Pat. No. 3,810,936, which is a continuation-in-part of Ser. No. 799,965, Feb. 17, 1969, abandoned.

[52] U.S. Cl..... 260/345.7; 260/345.8; 260/448.8 R; 260/468 D; 260/514 D
[51] Int. Cl.$^2$..................... C07F 7/18; C07D 309/06
[58] Field of Search......... 260/468 D, 514 D, 345.7, 260/345.8, 448.8 R

[56] References Cited
UNITED STATES PATENTS
3,532,721   10/1970   Finch .............................. 260/345.8

OTHER PUBLICATIONS
Organic Syntheses 49, p. 102 (1969).
Miyano et al., Chem. Comm. 180 (1973).
Finch et al. Tet. Letters, 4639 (1969).

*Primary Examiner*—Robert Gerstl
*Attorney, Agent, or Firm*—John A. Dhuey

[57] ABSTRACT

2-Formyl-3-protected hydroxy-5-oxocyclopent-1-eneheptanoic acid and its esters are stereoselectively reduced to the corresponding 2β-formyl-3α-protected hydroxy-5-oxocyclopentane-1α-heptanoic acid and esters with chromous sulfate. The compounds so produced are useful as intermediates to $PGE_1$ and its esters, which compounds exhibit hypotensive and smooth muscle-stimulating properties.

5 Claims, No Drawings

PROCESS FOR THE PRODUCTION OF 2β-FORMUL 3α-PROTECTED HYDROXY-5-OXOCYCLOPENTANE-1α-HEPTANOIC ACIDS AND ESTERS CORRESPONDING

This application is a continuation-in-part of my copending application Serial No. 187,853, filed October 8, 1971, now U.S. Pat. No. 3,810,936, which is a continuation-in-part of my application Serial No. 799,965 filed February 17, 1969, now abandoned.

The present invention is concerned with a novel process for the production of chemical compounds characterized by a cyclopentane structure. More particularly, it is concerned with the production of 2-formyl 3-protected hydroxy-5-oxocyclopentaneheptanoic acids and esters corresponding represented by the following structural formula.

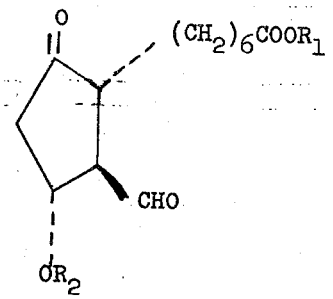

wherein $R_1$ is a lower alkyl radical containing 1-7 carbon atoms inclusive or a tetrahydropyran-2-yl, 4-(lower alkoxy)tetrahydropyran-4-yl or tri(lower alkyl)silyl radical and $R_2$ is a tetrahydropyran-2-yl, 4-(lower alkoxy)-tetrahydropyran-4-yl or a tri(lower alkyl)silyl radical, by contacting the corresponding $\Delta^{1,2}$ unsaturated compounds of the formula

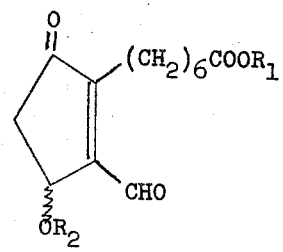

wherein the wavy line represents the optically active 3(R) isomer or the racemic mixture, with a chromous ion reducing agent.

The instant process is a particularly useful since the stereoisomers produced in major quantities are those which are analogous in configuration to natural $PGE_1$. Thus, the chromous sulfate reduction of the 2-formyl-3-protected hydroxy-5-oxocyclopent-1-eneheptanoic acid preferentially affords, as the major product, racemic 2β-formyl-3α-protected hydroxy-5-oxocyclopentane1α-heptanoic acid.

Preferred chromous ion reducing agents are chromous sulfate, chromous acetate and chromous perchlorate, with chromous sulfate being particularly preferred.

The lower alkyl radicals represented by $R_1$ and $R_2$ are typified by methyl, ethyl, propyl, butyl, pentyl, hexyl, heptyl and the branched-chain groups isomeric therewith.

Illustrative of the lower alkoxy radicals represented herein containing 1-7 carbon atoms inclusive are methoxy, ethoxy, propoxy, butoxy, isopropoxy and the like.

It is understood that other protecting groups, equivalent to those described herein, may be utilized in the instant process. However, those described herein are preferred.

Reaction temperatures and length of reaction times are not deemed critical for the stereoselective operation of the process. Such temperatures and times will be obvious to those skilled in the art from the examples which follow and may be selected according to standard chemical manufacturing procedures. Useful solvents in which the reduction may be run include dimethylsulfoxide, aqueous dimethylformamide, aqueous dioxane and aqueous tetrahydrofuran but are not limited thereto.

Materials suitable for the manufacture of the starting materials employed in this invention are styrylglyoxal, conveniently prepared by the selenous acid oxidation of 4-phenyl-3-buten-2-one, and the dialkyl esters of 3-oxoundecane-1,11-dioic acid. Dimethyl 3-oxoundecane-1,11-dioate is thus saponified with potassium hydroxide and the resulting dicarboxylic acid is allowed to react with styrylglyoxal, thus affording 14-phenyl-9,12-dioxo-11-hydroxytetradec-13-enoic acid. Cyclization of the latter intermediate in the presence of potassium hydroxide results in 3-hydroxy-5-oxo-2-styrylcyclopent-1-eneheptanoic acid.

The 2-(α,β-dihydroxyphenethyl) derivatives are readily obtained by hydroxylation of the corresponding 2-styryl compounds. A convenient reagent is osmium tetroxide. Methyl 3-hydroxy-5-oxo-2-styrylcyclopent-1-eneheptanoate is thus contacted at room temperature with osmium tetroxide in dioxane to produce methyl 3-hydroxy-5-oxo-2-(α,β-dihydroxyphenethyl)-cyclopent-1-eneheptanoate.

The 2-formyl compounds useful in this invention are then conveniently prepared by cleaving the glycol structure of the corresponding 2-(α,β-dihydroxyphenethyl) substances. Methyl 3-hydroxy-5-oxo-2-(αβ-dihydroxyphenethyl)cyclopent-1-eneheptanoate in ethanol is contacted with aqueous sodium periodate, thus affording methyl 3-hydroxy-2-formyl-5-oxocyclopent-1-eneheptanoate. The 2-formyl compounds are alternatively produced from the corresponding 2-styryl derivatives by combining the hydroxylation and cleavage processes. Methyl 3-hydroxy-5-oxo-2-styrylcyclopent-1-eneheptanoate in aqueous dioxane is thus allowed to react with osmium tetroxide and sodium periodate to afford methyl 2-formyl-3-hydroxy-5-oxocyclopent-1-eneheptanoate.

The optically active 2-formyl-3-oxygenated compounds are prepared from the racemic 2-styryl-3-hydroxy compounds by resolution of the latter compounds with either (+) or (−)-0-methylmandelyl chloride, thus forming the isomeric 2-styryl-3-((−)-0-methylmandeloxy) derivatives or the corresponding (+) derivatives, which can be separated chromatographically. Treatment of the latter compounds with base, such as potassium carbonate, affords the 2-styryl-3α-hydroxy and 2-styryl-3β-hydroxy derivatives which can be hydroxylated and cleaved in the manner described previously to produce the optically active 2-formyl-3α-hydroxy and 2-formyl-3β-hydroxy compounds, respectively. Typically, 3-hydroxy-5-oxo-2-styrylcyclopent-1-eneheptanoic acid is contacted with (−)-0-methylmandelyl chloride to produce 3β-((−)-0-methylmandeloxy)-5-oxo-2styrylcyclopent-1-eneheptanoic acid and 3α-((−)-0-methylmandeloxy)-5-oxo-2-styrylcyclopent-1-eneheptanoic acid, which are separated chromatographically on silicic acid. Treatment of the separated optical isomers with potassium carbonate affords (+)-3β-hydroxy-5-oxo-2-styrylcyclopent1-eneheptanoic acid and (−)-3α-hydroxy-5-oxo-2-styrylcyclopent-1-eneheptanoic acid, respectively. Subsequent hydroxylation with osmium tetroxide and cleavage with sodium periodate yields (+)-2-formyl-3β-hydroxy-5-oxocyclopent-1-eneheptanoic acid and (−)-2-formyl-3α-hydroxy-5-oxocyclopent-1-eneheptanoic acid, respectively.

The 2-formyl-3-hydroxy compounds produced by the methods outlined above then are allowed to react with dihydro-γ-pyran, a 4-alkoxy-2,3-dihydro-α-pyran or a trialkylsilyl halide to produce the intermediates of formula (II). Those reactions are suitably carried out in solvents such as methylene chloride, tetrahydrofuran, pyridine and the like. Preferably, a catalytic amount of p-toluenesulfonic acid is added to the reaction mixture to promote the formation of the pyranyl ethers. Also, it is desirable to add 1,1,3,3-tetramethyl-1,3-di(t-butyl)-silizane to the solvent when the trialkylsilyl ethers are formed with tetrahydrofuran as solvent. Typical of the above reactions are those of 2-formyl-3-hydroxy-5-oxocyclopent-1-eneheptanoic acid with dihydro-γ-pyran 4-methoxy-2,3-dihydro-α-pyran and dimethyl-t-butylsilyl chloride to produce, respectively, 2-formyl-3-(tetrahydropyran-2′-yl)oxy-5-oxocyclopent-1-eneheptanoic acid, 2-formyl-3-(4′-methoxytetrahydropyran-4′-yl)oxy-5-oxocyclopent-1-eneheptanoic acid and 2-formyl-3-(dimethyl-t-butylsilyl)oxy-5oxocyclopent-1-eneheptanoic acid.

The compounds of formula (II) are reduced with chromous sulfate, chromous acetate or chromous perchlorate to produce the compounds of formula (I) as major products. For example, 2-formyl-3-(tetrahydropyran-2′yl)oxy-5-oxocyclopent-1-eneheptanoic acid is treated with chromous sulfate to produce as the major product, 2β-formyl-3α-(tetrahydropyran-2′-yl)oxy-5-oxocyclopentane-1α-heptanoic acid, accompanied by the minor product, 2β-formyl-3β-(tetrahydropyran-2′-yl)oxy-5-oxocyclopentane-1α-heptanoic acid. Those compounds may be separated chromatographically or may be reacted further as crude products. Condensation of compounds of formula (I) with triaryl, e.g. triphenyl or tritolyl, or trialkyl n-hexanoylmethylene phosphorane affords the 11-protected hydroxy-9, 15-dioxoprost-13-trans-enoic acid or esters, which then are reduced to yield the 15(S)-hydroxy derivatives. Regeneration of the hydroxy moiety by hydrolysis then affords racemic PGE$_1$ or its esters. Typically, crude 2β-formyl-3α-(tetrahydropyran-2′-yl)oxy-5-oxocyclopentane-1α-heptanoic acid is treated with triphenyl n-hexanoylmethylene phosphorane to yield 11α-(tetrahydropyran-2′-yl)oxy-9,15-dioxoprost-13-trans-enoic acid. Then that product is reduced with sodium borohydride to yield 11α-(tetrahydropyran-2′-yl)oxy-15(S)-hydroxy-9oxoprost-13-trans-enoic acid which is hydrolyzed with aqueous acetic acid to yield racemic 11α,15(S)-dihydroxy9-oxoprost-13-trans-enoic acid.

The compounds produced by this invention are useful as intermediates in the manufacture of PGE$_1$, its esters and their optically active isomers. Those compounds possess well known pharmacological activity and are useful as hypotensive and smooth-muscle stimulating agents.

The following examples describe in detail the process illustrative of the present invention. The invention, however, is not to be construed as limited thereby either in spirit or in scope since it will be apparent to those skilled in the art that many modifications both of materials and of methods may be practiced without departing from the purpose and intent of this disclosure. It is understood that the procedures employing racemic mixtures in the following examples are applicable to the optical isomers as well. Throughout these examples temperatures are given in degrees Centigrade and relative amounts of materials in parts by weight except as otherwise noted.

EXAMPLE 1

A solution containing 100 parts of 4-phenyl-3-buten-2-one, 106 parts of selenous acid, 160 parts of dioxane and 20 parts of water is heated to the reflux temperature. After the initial vigorous reaction has subsided, the mixture is heated at that temperature for an additional 30 minutes. The supernatant is then decanted from the metallic selenium and is concentrated under reduced pressure. Distillation of the residue under reduced pressure affords, as a yellow oil, styrylglyoxal, boiling at about 120° at 2.5 mm. pressure.

EXAMPLE 2

A solution of 38.2 parts of dimethyl 3-oxoundecane-1,11-dioate in 200 parts by volume of 10% aqueous potassium hydroxide is stored at 0–5° for about 3 days, then is adjusted to pH 5 by the addition of concentrated aqueous citric acid. To that mixture is added to a solution which is prepared by heating 21.9 parts of styrylglyoxal in 50 parts by volume of 50% aqueous methanol at 65°–75° for about 20 minutes, then adding 60 parts of methanol. To the resulting reaction mixture is added 30 parts by volume of 1 M pH 4.5–5.0 citrate buffer and stirring at room temperature is continued for about 3 hours, during which time carbon dioxide gas is evolved. The precipitated product is collected by filtration, thus affording the half potassium salt of dl-14-phenyl-9,12-dioxo-11-hydroxytetradec-13-enoic acid, melting at about 105°. Further purification by recrystallization from methanol affords the pure compound, melting at about 107.5°.

The latter half potassium salt is dissolved in water and the resulting aqueous solution is acidified by the addition of dilute hydrochloric acid. The resulting acidic mixture is extracted with ether and the ether layer is separated, washed with water, dried over anhydrous sodium sulfate and concentrated to dryness. The resulting solid residue is purified by recrystallization from chloroform-ether to yield dl-14-phenyl-9,12-dioxo-11-hdroxytetradec-13-enoic acid, melting at about 81.5°–83°.

EXAMPLE 3

To 3000 parts by volume of an aqueous solution containing 6.7 parts of potassium hydroxide is added, with stirring at 21°–23° over a period of about 2 ¼ hours, a solution of 10.4 parts of dl-14-phenyl-9,12-dioxo-11-hydroxytetradec-13-enoic acid in 187 parts of chloroform. After completion of the addition, the reaction mixture is stirred for an additional 2 hours, then is made acidic by adding 10 parts of oxalic acid dihydrate. The acidic mixture is extracted with chloroform and the organic layer is washed with dilute aqueous sodium chloride, then dried over anhydrous sodium sulfate and concentrated to dryness under reduced pressure. The resulting residue is recrystallized first from benzene, then from chloroform-ether to yield dl-3-hydroxy-5-oxo-2-styrylcyclopent-1-eneheptanoic acid, which displays a melting point at about 118°. This compound displays an ultraviolet absorption maximum at about 325 millimicrons with a molecular extinction coefficient of about 36,400.

EXAMPLE 4

A mixture containing 44.3 parts of dl-3-hydroxy15-oxo-2-styrylcyclopent-1-eneheptanoic acid, 11.3 parts of diazomethane and 700 parts of ether is kept at room temperature for about 5 minutes, at the end of which time acetic acid is added in order to destroy the excess reagent. The resulting mixture is then washed with aqueous sodium bicarbonate, dried over anhydrous sodium sulfate and stripped of solvent by distillation under reduced pressure. The residue is purified by chromatography, first on silica gel followed by elution with 50% ethyl acetate in benzene, then by dry chromatography on silica gel containing 8% water, also using 50% ethyl acetate in benzene, thus affording dl-methyl 3-hydroxy-5-oxo-2-styrylcyclopent-1-eneheptanoate. This compound is characterized by infrared absorption maxima, in chloroform, at about 2.75, 2.87, 5.76, 5.88 and 6.17 microns and by an ultraviolet absorption maximum at about 325 millimicrons with a molecular extinction coefficient of about 36,000.

EXAMPLE 5

A mixture consisting of 13 parts of dl-3-hydroxy-5-oxo-2-styrylcyclopent-1-eneheptanoic acid, 17.8 parts of sodium periodate, 55 parts of water, 160 parts of dioxane and 2 parts of a 2% osmium tetroxide in dioxane solution is stirred under nitrogen at room temperature for about 4 hours. That reaction mixture is then extracted with ether and the ether layer is separated and extracted several times with 0.5% aqueous sodium chloride. The salt extracts are saturated with sodium chloride, then extracted with ether. The ether layer is separated, dried over anhydrous sodium sulfate, concentrated and dried under reduced pressure to afford dl-2-formyl-3-hydroxy-5-oxocyclopent-1-eneheptanoic acid, characterized by an ultraviolet absorption maximum at about 228 millimicrons with a molecular extinction coefficient of about 10,100.

EXAMPLE 6

A mixture of 13.5 parts of dl-methyl 3-hydroxy-5-oxo-2-styrylcyclopent-1-eneheptanoate, 17.8 parts of sodium periodate, 55 parts of water, 160 parts of dioxane and 2 parts by volume of a 2% osmium tetroxide in dioxane solution is stirred at room temperature under nitrogen for about 4 hours. The reaction mixture is extracted with ether and the ether solution is dried over anhydrous sodium sulfate, then concentrated to dryness under reduced pressure. The resulting residue is purified by dry column chromatography on silica gel containing 8% of water, using 50% ethyl acetate in benzene, thus affording dl-methyl 2-formyl-3-hydroxy-5-oxocyclopent-1-eneheptanoate, characterized by an ultraviolet absorption maximum at about 228 millimicrons with a molecular extinction coefficient of about 10,200.

EXAMPLE 7

Substitution of an equivalent quantity of diazoethane in the procedure of Example 4 yields dl-ethyl 3-hydroxy-5-oxo-2-styrylcyclopent-1-eneheptanoate.

EXAMPLE 8

By substituting an equivalent quantity of dl-ethyl 3-hydroxy-5-oxo-2styrylcyclopent-1-eneheptanoate in the procedure of Example 6, there is afforded dl-ethyl 2-formyl-3-hydroxy-5-oxocyclopent-1-eneheptanoate.

EXAMPLE 9

To a solution of 2 parts of dl-2-formyl-3-hydroxy-5-oxocyclopent-1-eneheptanoic acid and 1 part by volume of dihydropyran in 6.7 parts of methylene chloride is added a solution containing 0.02 part of p-toluenesulfonic acid in 0.18 part of tetrahydrofuran. A rapid exothermic reaction then ensues. After completion of the reaction, the mixture is diluted with 400 parts of methylene chloride, then washed with aqueous sodium sulfate and dried over anhydrous sodium sulfate. Concentration of the dried mixture under reduced pressure affords, as a pale yellow oil, dl-2-formyl-3-(tetrahydropyran-2'-yl)oxy-5-oxocyclopent-1-eneheptanoic acid.

To the crude reaction mixture containing dl-2-formyl-3-(tetrahydropyran-2'-yl)oxy-5-oxocyclopent-1-eneheptanoic acid described in the previous paragraph is added 32 parts by volume of chromous sulfate solution, prepared from chromic sulfate as described in Organic Synthesis, Volume 49, page 98. The resulting reaction mixture is stirred under nitrogen for about 30 minutes, at the end of which time 3 parts of ammonium sulfate and 25 parts of sucrose are added and the mixture is finally acidified by the addition of 1 M aqueous citric acid. That mixture is extracted with ether and the ether extract is separated, washed successively with saturated ammonium chloride and saturated sodium chloride, then dried over anhydrous sodium sulfate and concentrated under reduced pressure to yield, as the major product, dl-2$\beta$-formyl-3$\alpha$-(tetrahydropyran-2'-yl)oxy-5-oxocyclopentane-1$\alpha$-heptanoic acid. The corresponding 3$\beta$-tetrahydropyran 2'-yl ether is obtained as the minor product.

A solution containing dl-2$\beta$-formyl-3$\alpha$-(tetrahydropyran-2'-yl)oxy-5-oxocyclopentane-1$\alpha$-heptanoic acid in an acetic acid:water:tetrahydrofuran (20:10:3) mixture is stored at 38°–40° for about 3 hours, then is concentrated to dryness under reduced pressure to afford dl-2$\beta$-formyl-3$\alpha$-hydroxy-5-oxocyclopentane-1$\alpha$-heptanoic acid.

EXAMPLE 10

A solution containing 2.2 parts of dl-2$\beta$-formyl-3$\alpha$-(tetrahydropyran-2'-yl)oxy-5-oxocyclopentane-1$\alpha$-heptanoic acid and 5 parts of triphenyl n-hexanoylmethylene phosphorane in 101 parts of benzene is heated at the reflux temperature for about 4 hours, then is cooled, washed successively with aqueous citric acid and aqueous sodium chloride, then dried over anhydrous sodium sulfate and chromatographed on a silicic acid column. Elution of the column with 15% ethyl acetate in benzene affords dl-9-oxo-11$\alpha$-(tetrahydropyran-2'-yl)oxy-15-oxoprost-13-trans-enoic acid. Obtained as a minor product is the corresponding 11$\beta$-isomer, which is more polar on thin layer chromatogram using a silica gel plate with a benzene:ethyl acetate:acetic acid (50:50:2) mixture as the developing solvent.

The procedure of the preceding paragraph is repeated starting with 2.2 parts of dl-2β-formyl-3α-(tetrahydropyran-2'-yl)oxy-5-oxocyclopentane-1α-heptanoic acid and the washed and dried benzene solution is used as such without chromatographic separation. That solution is warmed with 150 parts by volume of an acetic acid:water:tetrahydrofuran (20:10:3) mixture at about 38°–40° for approximately 4 hours. Elution of that mixture with water affords an aqueous solution, which is extracted with benzene. The benzene extract is washed with aqueous sodium chloride, dried over anhydrous sodium sulfate and concentrated under reduced pressure, then purified by chromatography on silicic acid to yield dl-9-oxo-11α-hydroxy-15-oxoprost-13-trans-enoic acid.

EXAMPLE 11

A mixture consisting of 14 parts of crude dl-2β-formyl-3α-(tetrahydropyran-2'yl) oxy-5-oxocyclopentane-1α-heptanoic acid, 50 parts of triphenyl n-hexanoylmethylene phosphorane and 264 parts of benzene is heated at reflux temperature for 5 hours. After the solution is cooled, the organic layer is washed with cold 3% citric acid, 2% sodium chloride solution, dried over anhydrous sodium sulfate and concentrated under reduced pressure. The material which remains is chromatographed on silicic acid and eluted with 15% ethyl acetate in benzene to afford successive fractions of dl-11α-(tetrahydropyran-2'-yl)oxy-9,15-dioxoprost-13-trans-enoic acid, dl-11β-(tetrahydropyran-2'-yl)oxy-9,15-dioxoprost-13-trans-enoic acid and triphenyl phosphine oxide. The ratio of the 11α-epimer to the 11β-epimer is about 4:1.

EXAMPLE 12

44.0 Parts of crude dl-2β-formyl-3α-(tetrahydropyran-2'-yl)oxy-5-oxocyclopentane-1α-heptanoic acid is treated in the same manner as in Example 11. However, upon chromatography, there is obtained 2 fractions consisting of dl-11α-(tetrahydropyran-2'-yl)oxy-9,15-dioxoprost-13-trans-enoic acid and a mixture of dl-11α-(tetrahydropyran-2'-yl)oxy-9,15-dioxoprost-13-transenoic acid and 11β-(tetrahydropyran-2'-yl)oxy-9,15-dioxoprost-13-trans-enoic acid.

A solution of dl-11α-(tetrahydropyran-2'-yl)oxy-9,15-dioxoprost-13-trans-enoic acid in 75 parts by volume of a 20:10:3 acetic acid:water:tetrahydrofuran mixture is heated at 40° for 3 hours. Then that solution is poured onto ice and extracted with ether. The ethereal extract is washed with a 1% sodium chloride solution, dried over anhydrous sodium sulfate and concentrated to dryness under reduced pressure. The remaining material is chromatographed on silicic acid using 50% ethyl acetate in benzene as eluant to yield pure dl-11α-hydroxy-9,15-dioxoprost-13-trans-enoic acid.

8.3 Parts of the second fraction of dl-11α-(tetrahydropyran-2'-yl)oxy-9,15-dioxoprost-13-trans-enoic acid and dl-11β-(tetrahydropyran-2'-yl)oxy-9,15-dioxoprost-13-trans-enoic acid is hydrolyzed in the same manner as described above. The hydrolyzed mixture is then chromatographed on silicic acid using 50% ethyl acetate in benzene as eluant to afford successively dl-11β-hydroxy-9,15-dioxoprost-13-trans-enoic acid, a mixture of dl-11α-hydroxy-9,15-dioxoprost-13-trans-enoic acid and dl-11β-hydroxy-9,15-dioxoprost-13-trans-enoic acid and dl-11α-hydroxy-9,15-dioxoprost-13-trans-enoic acid.

EXAMPLE 13

A mixture of 2.2 parts of dl-2β-formyl-3α-(tetrahydropyran-2'-yl)oxy-5-oxocyclopentane-1α-heptanoic acid in 36 parts of dioxane and 101 parts of benzene is treated with 5 parts of triphenyl n-hexanoylmethylene phosphorane and boiled for 4 hours. After the reaction mixture is cooled, it is washed with a cold 5% citric acid solution and then a 1% sodium chloride solution. The reaction mixture is dried over anhydrous sodium sulfate and concentrated to dryness under reduced pressure. The crude condensation mixture which remains is hydrolyzed with 150 parts by volume of a 20:10:3 mixture of acetic acid:water:tetrahydrofuran at room temperature for about 18 hours. Then the solution is diluted with 300 parts of ice water and extracted with ether. The ethereal extracts are washed with cold 1% sodium chloride solution, dried over anhydrous sodium sulfate, concentrated to dryness and chromatographed on a partition column. That partition column is made by shaking together 15 parts by volume of benzene, 5 parts by volume of methanol and 2 parts of water. The two layers which form are separated, with the upper layer being used for elution and the lower layer being used as the stationary phase. The column is prepared by thoroughly mixing 75 parts of silicic acid and 75 parts by volume of the lower phase and passing that mixture into a column containing the upper phase. Then the column is washed with 500 parts by volume of the upper phase before use. The crude product is placed on the column and, after elution with the upper phase, the following fractions are obtained successively: triphenylphosphine oxide, a small amount of dl-11β-hydroxy-9,15-dioxoprost-trans-13-enoic acid and finally dl-11α-hydroxy-9,15-dioxoprost-trans-13-enoic acid.

EXAMPLE 14

To a chilled solution of 0.208 part of dl-11α-(tetrahydropyran-2'-yl)oxy-9,15-dioxoprost-13-trans-enoic acid in 17.4 parts of methanol is added 0.048 part by volume of triethylamine followed by 0.94 part of an aqueous sodium borohydride solution prepared from 0.058 part of sodium borohydride and 3.0 parts of water. That mixture is allowed to react, while being cooled by an ice bath, for 2 hours. Then the excess sodium borohydride is destroyed with acetone and the reaction mixture is diluted with ether. The ethereal solution is washed successively with cold 2% citric acid, 2% sodium chloride, and then dried over anhydrous sodium sulfate and concentrated under reduced pressure. The remaining material is chromatographed on silicic acid with 20% ethyl acetate in benzene being used as eluant. That separation affords fractions consisting of dl-11α-(tetrahydropyran-2'-yl)oxy-9,15-dioxoprost-13-trans-enoic acid, dl-9α-hydroxy-11α-(tetrahydropyran-2'-yl)oxy-15-oxoprost-13-trans-enoic acid and an approximately 50:50 mixture of dl-11α-(tetrahydropyran-2'-yl)oxy-15(S)-hydroxy-9-oxoprost-13-trans-enoic acid and dl-9β-hydroxy-11α-(tetrahydropyran-2'-yl)oxy-15-oxoprost-13-trans-enoic acid.

The fraction consisting of dl-9α-hydroxy-11α-(tetrahydropyran-2'-yl)oxy-15-oxoprost-13-trans-enoic acid is treated with 1 part by volume of a 20:10:3 acetic acid:water:tetrahydrofuran solution and heated at 40° for 3 hours. Then it is chromatographed on silicic acid and recrystallized from ethyl acetate-cyclohexane to afford pure dl-9α,11α-dihydroxy-15-oxoprost-13-trans-enoic acid, melting at about 81°–82° and displaying an absorption band in the ultraviolet spectrum at about 233 millimicrons with a molecular extinction coefficient of about 13,500.

The fraction consisting of the above 50:50 mixture is likewise hydrolyzed and then chromatographed on the partition column described in Example 13, to yield successive fractions of dl-11α,15(S)-dihydroxy-9-oxoprost-13-trans-enoic acid and dl-9β,11α-dihydroxy-15-oxoprost-13-trans-enoic acid. The initial fraction consisting of dl-PGE$_1$ melts at about 112°–113° and exhibits an identical 100 megaHertz nuclear magnetic resonance spectrum in deuteriomethanol as well as in deuteriochloroform with that of natural PGE$_1$. The latter fraction consisting of dl-9β,11α-dihydroxy-15-oxoprost-13-trans-enoic acid is recovered as an oil and exhibits absorption in the ultraviolet spectrum in methanol at about 232 millimicrons with a molecular extinction coefficient of 13,100.

EXAMPLE 15

A solution of 2.0 parts of dl-2-formyl-3-hydroxy-5-oxocyclopent-1-eneheptanoic acid in 8.9 parts of tetrahydrofuran is treated with 1.0 part of dimethyl-t-butylsilyl chloride and 1.0 part of 1,1,3,3-tetramethyl-1,3-di-t-butylsilizane. The reaction mixture is warmed to 40° and allowed to react for 20 hours. Then it is concentrated under a nitrogen stream and chromatographed on silicic acid to yield as the major product dl-2-formyl-3α-(dimethyl-t-butylsilyl)oxy-5-oxocyclopent-1-eneheptanoic acid.

When the crude reaction mixture is allowed to react with chromous sulfate in the manner described in Example 9, there is produced as the major product, dl-2β-formyl-3α-(dimethyl-t-butylsilyl)oxy-5-oxocyclopentane-1α-heptanoic acid. The corresponding 3β-isomer is obtained as the minor product.

EXAMPLE 16

A solution of 7.5 parts of dl-2β-formyl-3α-(dimethyl-t-butylsilyl)oxy-5-oxocyclopentane-1α-heptanoic acid and 15 parts of triphenyl n-hexanoylmethylene phosphorane in 220 parts of benzene is heated at reflux temperature for 5 hours. After the solution is cooled, it is treated according to the procedure described in Example 13. The desired product, dl-11α-(dimethyl-t-butylsilyl)oxy-9,15-dioxoprost-13-trans-enoic acid is eluted with 10% ethyl acetate in benzene on a silicic acid column. That isomer is followed by the dl-11β-(dimethyl-t-butylsilyl)oxy-9,15-dioxoprost-13-trans-enoic acid. The ratio of 11α-epimer to 11β-epimer is about 85:15.

A solution of 1 part of dl-11α-(dimethyl-t-butylsilyl)oxy-9,15-dioxoprost-13-trans-enoic acid in 20 parts of a 20:10:3 mixture of acetic acid:water:tetrahydrofuran is stored at room temperature for 40 hours. Then the hydrolysis product is treated according to the procedure described in Example 12 to produce dl-11α-hydroxy-9,15-dioxoprost-13-trans-enoic acid.

EXAMPLE 17

To a solution of 2.0 parts of dl-2-formyl-3-hydroxy-5-oxocyclopent-1-eneheptanoic acid and 1.0 part by volume of 4-methoxy-2,3-dihydro-α-pyran in 7 parts of methylene chloride is added a solution of 0.02 part of p-toluenesulfonic acid in 0.2 part of tetrahydrofuran. After completion of the reaction, the mixture is diluted with 400 parts of methylene chloride, then washed with cold aqueous sodium sulfate and dried over anhydrous sodium sulfate. Evaporation of the solvent under reduced pressure affords, as a pale yellow oil, 2-formyl-3-(4'-methoxytetrahydropyran-4'-yl)oxy-5-oxocyclopent-1-eneheptanoic acid.

EXAMPLE 18

A mixture consisting of 14 parts of crude dl-2β-formyl-3α-(tetrahydropyran-2'-yl)oxy-5-oxocyclopentane-1α-heptanoic acid, 40 parts of tri-n-butyl n-hexanoylmethylene phosphorane and 280 parts of ether is set aside for 18 hours. Then the reaction mixture is washed successively with cold 3% citric acid and 2% sodium chloride solution, dried over anhydrous sodium sulfate and concentrated to dryness under reduced pressure. The material which remains is chromatographed on silicic acid and eluted with 15% ethyl acetate in benzene to afford successive fractions of dl-11α-(tetrahydropyran-2'-yl)oxy-9,15-dioxoprost-13-trans-enoic acid and dl-11β-(tetrahydropyran-2'-yl)oxy-9,15-dioxoprost-13-trans-enoic acid.

EXAMPLE 19

Substitution of an equivalent quantity of dl-methyl 2-formyl-3-hydroxy-5-oxocyclopent-1-eneheptanoate in the procedure of Example 9 and otherwise following the procedure of Example 9 affords crude dl-methyl 2β-formyl-3α-(tetrahydropyran-2'-yl)oxy-5-oxocyclopentane-1α-heptanoate.

EXAMPLE 20

A mixture of 3.3 parts of (−)-O-methylmandelic acid, 44 parts of benzene, and 9.67 parts of oxalyl chloride is heated at 60°–70° for about 90 minutes. After the solvent is removed under reduced pressure, the remaining residue is dissolved in 26.4 parts of benzene and again concentrated to dryness. The crude (−)-O-methylmandelyl chloride thus obtained is taken up in 17.6 parts of benzene and added to a cold solution of 5.5 parts of 3-hydroxy-5-oxo-2-styrylcyclopent-1-eneheptanoic acid dissolved in 9.82 parts of dry pyridine. That mixture is allowed to stand for about 16 hours at room temperature and then it is poured into a cold solution containing 40 parts of d-tartaric acid in 1350 parts of water. That mixture is extracted with ethyl acetate and the organic extracts are washed with water, dried over anhydrous sodium sulfate and concentrated to dryness. The oily residue which remains is dissolved in benzene and chromatographed on silicic acid. The initial fraction obtained upon elution with 15% ethyl acetate-85% benzene is recrystallized from benzene-hexane to give colorless crystals of 3β-((−)-O-methylmandeloxy)-5-oxo-2-styrylcyclopent-1-eneheptanoic acid, melting at about 122°–124° and displaying an optical rotation in methanol of about −22.2°. That compound is further characterized, in chloroform, by absorption maxima in the infrared spectrum at about 1750, 1710 and 1630 reciprocal centimeters and an ultraviolet absorption band, in methanol, at about 326 millimicrons wth a molecular extinction coefficient of about 36,000. The latter fraction, obtained upon elution with 15% ethyl acetate-85% benzene, is recrystallized from benzene-hexane to give colorless needles of 3α-((−)-O-methylmandeloxy)-5-oxo-2-styrylcyclopent-1-eneheptanoic acid, melting at about 96°–98° and displaying an optical rotation of about −84.2° in methanol. That compound absorbs in the infrared spectrum, in chloroform, at about 1750, 1710 and 1630 reciprocal centimeters and has an absorption band in the ultraviolet spectrum at about 326 millimicrons with a molecular extinction coefficient of about 35,000 in methanol.

EXAMPLE 21

A solution of 0.300 part of 3β-((−)-0-methylmandeloxy)-5-oxo-2-styrylcyclopent-1-eneheptanoic acid in 2.66 parts of tetrahydrofuran is added to 30 parts by volume of a 1% aqueous potassium carbonate solution. That mixture then is allowed to stand at room temperature under a nitrogen atmosphere in subdued light for about 3 days. The resulting solution is cooled in ice and acidified with dilute aqueous acetic acid. Then the product is isolated by filtration, taken up in ethyl acetate, washed with water, dried over anhydrous sodium sulfate, and dried under reduced pressure. The crude residue is dissolved in a small amount of 50% benzene-ethyl acetate and chromatographed on silicic acid suspended in 50% benzene-ethyl acetate. Elution with the same solvent yields the crude product which is recrystallized from benzene containing a small amount of ethyl acetate to give pure colorless crystals of (+)-3β-hydroxy-5-oxo-2-styrylcyclopent-1-eneheptanoic acid, melting at about 112°–114° and displaying an optical rotation in methanol of about +12.6°. That compound further displays, in methanol, an absorption band in the ultraviolet spectrum at about 326 millimicrons with a molecular extinction coefficient of about 35,600.

EXAMPLE 22

By substituting an equivalent quantity of 3α-((−)-0-methylmandeloxy)-5-oxo-2-styrylcyclopent-1-eneheptanoic acid in the procedure of Example 21, there is obtained (−)-3α-hydroxy-5-oxo-2-styrylcyclopent-1-eneheptanoic acid, melting at about 112°–113° and displaying an optical rotation in methanol of about −16.5°.

EXAMPLE 23

When an equivalent quantity of (+)-3β-hydroxy-5-oxo-2-styrylcyclopent-1-eneheptanoic acid is substituted in the procedure of Example 5, there is produced (+)-2-formyl-3β-hydroxy-5-oxocyclopent-1-eneheptanoic acid.

EXAMPLE 24

Substitution of an equivalent quantity of (−)-3α-hydroxy-5-oxo-2-styrylcyclopent-1-eneheptanoic acid in the procedure of Example 5 and otherwise following the procedure of Example 5 yields (−)-2-formyl-3α-hydroxy-5-oxocyclopent-1-eneheptanoic acid.

EXAMPLE 25

When an equivalent quantity of (+)-0-methylmandelic acid is substituted in the procedure of Example 20, there are produced 3β-((+)-0-methylmandeloxy)-5-oxo-2-styrylcyclopent-1eneheptanoic acid, displaying an optical rotation in methanol of +84°, and 3α-((+)-0-methylmandeloxy)-5-oxo-2-styrylcyclopent-1-eneheptanoic acid, displaying an optical rotation in methanol of +20°.

EXAMPLE 26

When an equivalent quantity of crude dl-methyl 2β-formyl-3α-(tetrahydropyran-2′-yl)oxy-5-oxocyclopentane-1α-heptanoate is substituted in the procedure of Example 11, there is obtained dl-methyl 11α-(tetrahydropyran-2′-yl)oxy-9,15-dioxoprost-13-trans-enoate, as the major product, and dl-methyl 11β-(tetrahydropyran-2′-yl)oxy-9,15-dioxoprost-13-trans-enoate, as the minor product.

What is claimed is:

1. A compound of the formula

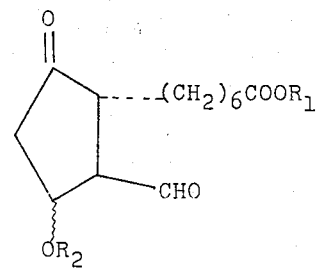

wherein $R_1$ is hydrogen or a lower alkyl, tetrahydropyran-2-yl,4-(lower alkoxy)tetrahydropyran-4-yl or tri(-lower alkyl)silyl radical, $R_2$ is a tetrahydropryan-2-yl,4-(lower alkoxy)tetrahydropryan-4-yl or tri(lower alkyl)-silyl radical and the wavy line represents the racemic mixture or the optically active 3(R) isomer.

2. A process for the production of a compound of the formula

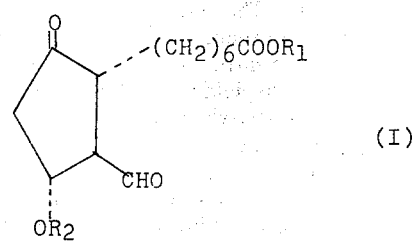

(I)

wherein $R_1$ is hydrogen, a lower alkyl, tetrahydropyran-2-yl, 4-(lower alkoxy)tetrahydropyran-4-yl or tri(lower alkyl)silyl radical and $R_2$ is a tetrahydropyran-2-yl, 4-(lower alkoxy)tetrahydropyran-4-yl or tri(lower alkyl)silyl radical which comprises contacting a compound of the formula

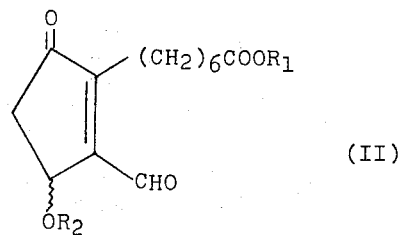

(II)

wherein $R_1$ and $R_2$ are defined as above and the wavy line represents the racemic (RS) compound or the optically active R isomer, with chromous sulfate, chromous acetate or chromous perchlorate reducing agent, wherein the molar ratio of reducing agent to compound of formula II is about 2:1

3. A process as in claim 1, wherein the compound of formula II is racemic and the reducing agent is chromous sulfate.

4. A process as in claim 1 which comprises contacting a racemic compound of the formula

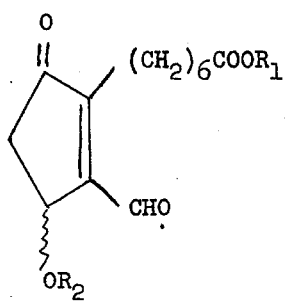

wherein $R_1$ is hydrogen or a lower alkyl tetrahydropyran-2-yl radical and $R_2$ is a tetrahydropyran-2-yl radical, with chromous sulfate.

5. A process as in claim 1 which comprises contacting dl-2-formyl-3-(tetrahydropyran-2-yl)oxy-5-oxocyclopent-1-eneheptanoic acid with chromous sulfate, thereby forming dl-2$\beta$-formyl-3$\alpha$-(tetrahydropyran-2-yl)-oxy-5-oxocyclopentane-1$\alpha$-heptanoic acid.

* * * * *